United States Patent [19]

Wolanin

[11] Patent Number: 5,270,301

[45] Date of Patent: Dec. 14, 1993

[54] FLUORO-AMIDE DERIVATIVES

[75] Inventor: Donald J. Wolanin, Wilmington, Del.

[73] Assignee: ICI Americas Inc., Wilmington, Del.

[21] Appl. No.: 519,618

[22] Filed: May 7, 1990

[30] Foreign Application Priority Data

May 8, 1989 [GB] United Kingdom ............... 8910547

[51] Int. Cl.⁵ ............... A61K 37/02; A61K 31/505;
A61K 31/44; A61K 31/38; A61K 31/34;
C07D 239/02; C07D 213/06; C07D 213/46;
C07D 317/44; C07D 307/02

[52] U.S. Cl. ..................... 514/19; 514/256;
514/269; 514/274; 514/275; 514/336; 514/346;
514/352; 514/354; 514/355; 514/444; 514/445;
514/446; 514/447; 514/448; 514/471; 514/472;
514/473; 530/331; 544/298; 544/316; 544/330;
544/331; 544/332; 544/335; 546/283; 546/284;
546/291; 546/309; 546/314; 546/316; 549/444;
549/445; 549/446; 549/447; 549/448; 549/472;
549/473; 549/479; 549/480; 549/487; 564/91

[58] Field of Search ............... 564/91; 514/19, 471,
514/472, 473, 444, 445, 446, 447, 448, 256, 269,
274, 275, 336, 346, 352, 354, 355; 530/331;
549/472, 473, 479, 480, 487, 59, 60, 62, 67, 69,
76; 546/283, 284, 291, 309, 314, 316

[56] References Cited

U.S. PATENT DOCUMENTS

| 4,256,761 | 3/1981 | Suh et al. | 424/282 |
| 4,880,780 | 11/1989 | Trainer et al. | 514/18 |
| 4,910,190 | 3/1990 | Bergeson et al. | 514/19 |
| 4,923,890 | 5/1990 | Trainor et al. | 424/46 |

FOREIGN PATENT DOCUMENTS

| 0249349 | 12/1987 | European Pat. Off. | 424/282 |
| 0276101 | 7/1988 | European Pat. Off. | 424/46 |
| 0291234 | 11/1988 | European Pat. Off. | 514/19 |
| 0369391 | 5/1990 | European Pat. Off. | 530/331 |

OTHER PUBLICATIONS

J. L. Stanton et al., J. Med. Chem. (1983) 26, 1267–1277.
J. T. Suh et al., J. Med. Chem. (1985) 28, 57–66.
S. M. Weldon et al., FASEB J. (1990) 4 (4), Abstract 5212.

Primary Examiner—Mary C. Lee
Assistant Examiner—Joseph K. McKane
Attorney, Agent, or Firm—Thomas E. Jackson

[57] ABSTRACT

The present invention relates to certain fluoro-amide derivatives, as described herein, which are human leukocyte elastase (HLE) inhibitors making them useful whenever such inhibition is desired, such as for research tools in pharmacological, diagnostic and related studies and in the treatment of diseases in mammals in which HLE is implicated, including treatment of tissue degenerative diseases such as pulmonary emphysema. The invention also includes intermediates useful in the synthesis of these fluoro-amide derivatives, processes for preparing them, pharmaceutical compositions containing such peptide derivatives and methods for their use.

12 Claims, No Drawings

FLUORO-AMIDE DERIVATIVES

The present invention relates to certain fluoro-amide derivatives, in particular, certain tripeptidoyl difluoroacetamide derivatives, which are human leukocyte elastase (HLE) inhibitors making them useful whenever such inhibition is desired, such as for research tools in pharmacological, diagnostic and related studies and in the treatment of disease in mammals in which HLE is implicated, including treatment of tissue degenerative diseases such as pulmonary emphysema. The invention also includes intermediates useful in the synthesis of these fluoro-amide derivatives, processes for preparing them, pharmaceutical compositions containing such fluoro-amide derivatives and methods for their use.

In European Patent Application, Publication Number 204 571 A2 are disclosed a series of peptidoyl difluoroacetamide derivatives which are HLE inhibitors. I have now discovered a series of tripeptidovl difluoroacetamide derivatives which contain an N-cyclopentylglycyl group at the P2-position and which unexpectedly possess inhibitory properties against HLE. In addition, the new derivatives have improved solution stability. This is the basis for my invention.

According to the invention there are provided compounds of formula I (Formula set out, together with other formulae referred to by Roman numerals, following the Examples) wherein:

A is selected from a group consisting of —CO—, —NH.CO— and —O.CO—;

L is selected from a group consisting of phenylene, (1-6C)alkanediyl, (2-6C)alkenediyl and phenylene(1-3-C)alkyl, optionally containing one double bond in the alkyl portion, with the condition that no carbon included in a double bond of an alkenediyl group or included in an optional double bond of a phenylenealkyl group be directly bonded to an oxygen or nitrogen atom of group A;

$R^4$ is selected from a group consisting of acylsulfonamide of formula $R^5.S(O_2).NH.CO$—, acylsulfonamide of formula $R^5.CO.NH.S(O_2)$—, sulfonylurea of formula $R^5.NH.CO.NH.S(O_2)$—, sulfonylurea of formula $R^5.S(O_2).NH.CO.NR^6$—, and trifluoromethylsulfonamide of formula $CF_3.S(O_2).NH$— wherein $R^5$ is selected from a group consisting of (1-10C)alkyl; trifluoromethyl; (3-10C)cycloalkyl; (6 or 10C)aryl optionally substituted by 1 to 3 members of a group consisting of halogeno, nitro, amino, dimethylamino, hydroxy, methyl, trifluoromethyl, carboxy, phenyl, and [(1-5C)alkylcarbonyl]amino; and an aromatic heterocyclic group defined as herein below in which up to 3 carbons of the aromatic system may bear a substituent group independently selected from a group consisting of halogeno and trifluoromethyl; and $R^6$ is hydrogen or methyl;

$R^A$ is hydrogen or methyl: and $R^B$ is selected from a group consisting of (1-10C)alkyl, (3-7C)cycloalkyl(1-6C)alkyl (wherein the cycloalkylalkyl group contains no more than about 10 carbon atoms), and a (1-6C)alkyl group bearing a substituent $R^C$ wherein $R^C$ is a phenyl group or a monocyclic aromatic heterocyclic group containing a 5- or 6-membered ring and consisting of from 1 to 5 carbons and from 1 to 4 heteroatoms each of which is selected independently from a group consisting of oxygen, sulfur, and nitrogen; and the pharmaceutically acceptable salts thereof.

In this specification, the following definitions are used, unless otherwise described:

Halogeno is fluoro, chloro, bromo or iodo.

Aromatic heterocyclic group means a monocyclic or fused bicyclic ring system of from 5 to 11 atoms containing at least one 5- or 6-membered aromatic ring and consisting of from 1 to 10 carbons and from 1 to 4 heteroatoms each of which is selected independently from a group consisting of oxygen, sulfur, and nitrogen.

Alkyl, alkanediyl, alkenediyl, etc. denote both straight and branched groups.

The radicals $R^4$, $R^B$ and L may contain chiral centers. The present invention includes compounds of formula I wherein chiral centers included in $R^4$, $R^B$ and L are of the R and/or S configurations. The radical L may contain a double bond; the present invention includes compounds of formula I wherein a double bond included in L is of the E and/or Z configuration.

The compounds of the invention of formula I can be viewed as tripeptidoyl difluoroacetamide derivatives. In general, the preferred compounds of the present invention are of the naturally occurring L-amino acid configuration at the chiral center identified by * in formula I. The methods of synthesis described below may provide a diastereomeric mixture as a result of the presence of products with both the R and the S configurations at the chiral center identified by # in formula 1. While these diastereomers may be separated, it is not necessary to do so. The preferred compounds are those assigned the S configuration at the chiral center identified by #.

As will be appreciated by those skilled in the art, the activity of the individual isomers is not the same, and it is therefore preferred to utilize the more active isomer. The present invention includes both the diastereomeric mixture and the active S and R isomers.

As will be appreciated by those skilled in the art, the difluoromethyl ketones of formula I can exist as solvates, particularly hydrates, represented by formula II, and these are encompassed by the present invention.

A particular value of $R^5$ when $R^5$ is (1-10C)alkyl is, for example, methyl, ethyl, propyl, isopropyl, t-butyl or 4-methylpentyl. A particular value of $R^5$ when $R^5$ is (3-10C)cycloalkyl is, for example, cyclopropyl, cyclopentyl, cyclohexyl, norbornyl, or adamantyl. A particular value for $R^5$ when $R^5$ is (6 or 10C)aryl is, for example, phenyl or naphthyl; a particular value for an optional substituent on aryl when the substituent is halogeno is, for example, fluoro, chloro or bromo and a particular value for an optional substituent on aryl when the substituent is [(1-5C)alkylcarbonyl]amino is, for example, formylamino, acetylamino, 2-methylpropanoylamino or 2,2-dimethylpropanoylamino. A particular value for $R^5$ when $R^5$ is an aromatic heterocyclic group is, for example, furyl, thienyl, pyridyl or pyrimidinyl; and a particular value for an optional substituent when the substituent is halogeno is, for example, fluoro, chloro or bromo.

A particular value for L when L is phenylene is, for example, p-phenylene or m-phenylene. A particular value for L when L is (1-6C)alkanediyl is, for example, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl or pentan-1,5-diyl. A particular value for L when L is (2-6C)alkenediyl is, for example, ethen-1,2-diyl, propen-1,2-diyl, propen-1,3-diyl, buten-1,4-diyl, but-2-en-1,4-diyl, penten-1,5-diyl or 3,3-dimethylpropen-1,3-diyl. A particular value for L when L is phenylene(1–3C)alkyl is, for example, p-phenylenemethyl, 2-(p-phenylene)ethyl or 2-(p-phenylene)-2-propyl; and when the phenylene-(1–3C)alkyl group contains an optional double bond, a particular value for L is, for example 2-(p-phenylene)ethenyl.

A particular value for $R^B$ when $R^B$ is (1–10C)alkyl is, for example, methyl, ethyl, propyl, butyl, 2-methylpropyl, pentyl, 3-methylbutyl, or hexyl. A particular value for $R^B$ when $R^B$ is (3–7C)-cycloalkyl (1–6C)alkyl is, for example cyclopropylmethyl, cyclopentylmethyl, cyclohexylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl or 4-cyclohexylbutyl. A particular value for $R^B$ when $R^B$ is a (1–6C)alkyl group bearing a substituent $R^C$ is, for example, benzyl, 2-phenylethyl, 3-phenylpropyl, 4-phenylbutyl, 2-thienylethyl or 2-furylethyl.

The particular values listed for radicals, substituents and ranges are for illustration only and do not exclude other defined values or other values within defined ranges for the radicals and substituents.

Values for $R^4$.L.A- in formula I of particular interest include for $R^4$: $R^5.S(O_2).NH.CO$—; for L: p-phenylene: and for A: —CO—. Values of $R^5$ of particular interest include phenyl and 4-chlorophenyl. A value of $R^4$ of particular interest is hydrogen. Values of $R^B$ of particular interest include propyl and 2-phenylethyl.

Specific compounds of formula I are described in the accompanying Examples. Compounds of special interest include: [4-[(4-chlorophenyl)sulfonylaminocarbonyl]benzoyl]-L-valyl-Nα-cyclopentyl-N-[3,3-difluoro-1-(1-methylethyl)-2,4-dioxo-4-(propylamino)-butyl]glycinamide.

The salts of the compounds of formula I include pharmaceutically acceptable base-addition salts such as those derived from alkali metal hydroxides such as sodium hydroxide, alkali metal carbonates and bicarbonates, alkaline earth hydroxides and organic amines. Such salts may be prepared by dissolving the heterocyclic ketone in a mixture of water and a water-miscible organic solvent, adding an aqueous solution of the base and recovering the salt from the aqueous solution.

The compounds of formula I may be made by processes which include processes known in the chemical art for the production of structurally analogous heterocyclic and peptidic compounds. Such processes for the manufacture of a compound of formula I as defined above are provided as further features of the invention and are illustrated by the following procedures in which the meanings of generic radicals are as defined above:

(A) Oxidizing a corresponding alcohol of formula III. Methods which are useful include the use of oxalyl chloride, dimethyl sulfoxide, and a tertiary amine; the use of acetic anhydride and dimethyl sulfoxide; the use of chromium trioxide pyridine complex in methylene chloride; and the use of Dess-Martin periodinane [1,1,1-triacetoxy-2,1-benzoxiodol-3(3H)-one] (method of Dess, D. B. et al, *J. Org. Chem.*, 48, 4155–56 (1983)). Generally, a preferred oxidant is Dess-Martin periodinane. An alternative preferred method of oxidation may be the use of potassium permanganate in a basic aqueous solution. When an alcohol of formula III contains a basic nitrogen, it is generally preferable to use an alternative method or to protect the basic nitrogen before oxidation and deprotect it after oxidation to provide the corresponding compound of formula I.

(B) For a compound of formula I wherein $R^4$ has the value $R^5.S(O_2).NH.CO$—, reacting a corresponding compound of formula IV wherein $R^7$ is carboxy (which compound is hereinafter referred to as "acid of formula IV") with a sulfonamide derivative of formula $R^5.SO_2.NH_2$ in the presence of a dehydrating agent or reacting a reactive derivative of an acid of formula IV with a sulfonamide, or a salt thereof, of formula $R^5SO_2.NH_2$. Thus, for example, a free acid of formula IV may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^5.SO_2.NH_2$ in the presence of a suitable solvent or diluent, for example, dichloromethane, at a temperature in the range of, for example, 0° to 50° C., but preferably at or near ambient temperature.

Alternatively, a reactive derivative of an acid of formula IV, for example, an acid halide (such as the acid chloride), acid anhydride or a mixed acid anhydride (such as that formed from N,N-diphenylcarbamic acid and the acid of formula IV by reaction of the sodium salt of the latter acid with N,N-diphenylcarbamoyl-pyridinium chloride), may be reacted with an alkali metal salt (such as the lithium, sodium or potassium salt) of the appropriate sulfonamide of formula $R^5.SO_2.NH_2$, conveniently at or near ambient temperature and in a suitable solvent or diluent, for example, tetrahydrofuran, N,N-dimethylformamide or dichloromethane.

(C) For a compound of formula I wherein $R^4$ has the value $R^5.CO.NH.S(O_2)$—, reacting a corresponding compound of formula IV in which $R^7$ has the value $H_2N.S(O_2)$— with an acid of formula $R^5.COOH$ using a similar method to one of those described above in part (B).

(D) For a compound of formula I wherein $R^4$ has the value $R^5.NH.CO.NH.S(O_2)$—, reacting a corresponding compound of formula IV in which $R^7$ has the value $H_2N.S(O_2)$— with an isocyanate of formula $R^5.NCO$. For example, an intermediate of formula IV in which $R^7$ is $H_2N.S(O_2)$— may be treated with phenylisocyanate to provide a corresponding product of formula I in which $R^5$ is phenyl.

(E) For a compound of formula I wherein $R^4$ has the value $R^5.S(O_2).NH.CO.NR^6$—, reacting a corresponding compound of formula IV in which $R^7$ has the value $HNR^6$— with a sulfonylisocyanate of formula $R^5.S(O_2).NCO$; or alternatively, for a compound in which $R^6$ has the value H, reacting a corresponding compound of formula IV in which $R^7$ has the value —NCO with a sulfonamide of formula $R^5.S(O_2).NH_2$. The reaction may be carried out, for example, at room temperature in a suitable inert organic solvent such as tetrahydrofuran or dichloromethane.

(F) For a compound of formula I wherein $R^4$ has the value $CF_3.S(O_2).NH$—, reacting a corresponding amine of formula IV in which $R^7$ has the value $H_2N$— with trifluoromethanesulfonic anhydride, for example, at 0° C. in an inert solvent such as dichloromethane.

(G) For a compound of formula I wherein A has the value —CO—, coupling an acid of formula $R^4.L.COOH$ (or a reactive derivative thereof) with an amino ketone of formula V. For example, the coupling may be carried out using 1-(3-dimethylaminopropyl)-3-ethylcarbodiimide hydrochloride and 4-dimethylaminopyridine or 1-hydroxybenzotriazole in an inert solvent such as tetrahydrofuran. Similarly, a compound of formula I wherein A has the value —NH.CO— or —O.CO — may be prepared from a corresponding amino ketone of formula V using a similar method to one described below for the preparation of a starting material alcohol of formula III from an amino alcohol of formula VII.

It may be desired to optionally use a protecting group during all or portions of the above described processes; the protecting group then may be removed when the final compound or a required starting material is to be formed.

Whereafter, for any of the above procedures, when a pharmaceutically acceptable salt is required, it may be obtained by reaction of the acidic form of a compound of formula I with a base affording a physiologically acceptable cation or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples.

As will be clear to one skilled in the art, a variety of sequences is available for preparation of the starting materials. According to one of the available routes, a key intermediate amino alcohol of formula VII may be prepared as shown in Scheme I (set out following Examples) wherein CBZ represents a benzyloxycarbonyl protecting group and as described in

EXAMPLE 1

Reformatsky reaction of CBZ-L-valinal with ethyl 2-bromo-2,2-difluoroacetate and zinc in tetrahydrofuran may be carried out either by using activated zinc and ultrasonic energy (sonication) or by refluxing to afford the corresponding hydroxy ester X as a mixture of diastereomers. (As will be clear to one skilled in the art, the diastereomeric alcohols may optionally be separated at any step in the preparation of a compound of formula I, or a mixture of diastereomers may be carried through until the hydroxy group is oxidized to a ketone.) Amidation of an ester of formula X with an amine of formula $HNR^A R^B$ by using a conventional method, followed by removal of the CBZ group by using a conventional method, may be carried out to afford a corresponding amino alcohol of formula XII.

Conversion of an amino alcohol of formula XII into a corresponding alcohol of formula XVI may be carried out by coupling the amino alcohol with an acid of formula XV using a conventional coupling procedure, such as, for example, using 1-(3-dimethylaminopropyl)-3-ethylcarbodiimide hydrochloride and 1-hydroxybenzotriazole in tetrahydrofuran, for example as described in Example 1, or by using bis(2-oxo-3-oxazolidinyl)-phosphinic chloride and triethylamine in dichloromethane. An alcohol of formula XVI may be converted into an amino alcohol of formula VII by removal of the CBZ-group using a conventional method, such as, for example, hydrogenolysis over a palladium on carbon catalyst at atmospheric pressure and ambient temperature in an appropriate solvent such as, for example, ethanol.

An amino alcohol of formula VII may be converted into a starting material of formula III by reacting the amino alcohol of formula VII with an appropriate acylating agent. For example, when A is —CO—, appropriate acylating agents are activated derivatives of acids of formula $R^4.L.COOH$, for example, activated derivatives thereof generated in situ when using conventional coupling reagents, such as, for example, 1-(3-dimethylaminopropyl)-3-ethylcarbodiimide hydrochloride and 1-hydroxybenzotriazole or 4-dimethylaminopyridine, as well as, for example, acid chlorides of formula $R^4.L.COCl$. When A is —NH.CO—, appropriate acylating agents include isocyanates of formula $R^4L.NCO$. When A is —O—CO—, appropriate acylating agents include chloroformates of formula $R^4.O.CO.Cl$. In general, the acylation is performed in an inert diluent or solvent, such as dichloromethane, tetrahydrofuran or dioxane, and at a temperature in the range of, for example, 0°–60° C. An organic or inorganic base such as triethylamine, 4-methylmorpholine, 4-dimethylaminopyridine, potassium carbonate or sodium hydroxide may also conveniently be used as an acid acceptor when appropriate.

Starting material ketones of formula IV may also be obtained from an intermediate alcohol of formula VII. Thus, for example, for a starting material of formula IV wherein $R^7$ has a value of $R^zO_2C-$, $H_2N.SO_2-$, or $R^6NH-$ and $R^z$ has a value defined below, an amino alcohol of formula VII may be converted into a corresponding alcohol of formula VI by using a method analogous to one described above for preparation of a compound of formula III and an analogous reagent, such as, for example $R^7.L.COOH$, $R^7.L.COCl$, $R^7.L.NCO$ or $R^7.L.O.COCl$. Then, by using a similar oxidation process to one described in process (A), an alcohol of formula VI may be oxidized to provide a starting material ketone of formula IV. A starting material ketone of formula IV wherein $R^7$ has a value of —NCO may be prepared from a corresponding ketone of formula IV wherein $R^7$ is carboxy by use of a modified Curtius reaction using, for example, diphenylphosphorylazide and triethylamine in benzene or toluene at 80° C. A starting material of formula IV wherein $R^7$ has the value carboxy may be prepared by decomposing a suitable, corresponding ester of formula IV wherein $R^7$ has the value $R^zO_2C-$ in which $R^z$ is a conveniently removed acid protecting group, for example, phenyl, benzyl, or (1-6C)alkyl optionally bearing an acetoxy, (1-4C)alkoxy or (1-4C)alkylthio substituent.

A particular value for $R^z$ is, for example, methyl, ethyl, propyl, t-butyl, acetoxymethyl, methoxymethyl, 2-methoxyethyl, methylthiomethyl, phenyl, or benzyl.

It will be appreciated that the decomposition of an ester of formula IV wherein $R^7$ is $R^zO_2C-$ may be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Alternatively, in certain circumstances, for example, when $R^z$ is t-butyl, it may be preferred to carry out the decomposition using acid catalysis, for example, by treating an ester of formula IV with, for example, trifluoroacetic acid at a temperature of, for example, 0°–40° C., in a suitable solvent or diluent such as dichloromethane. In addition, when $R^z$ is t-butyl, the decomposition may be performed, for example, by using trimethylsilyl triflate and then water, in a conventional manner. Still further, in certain circumstances, for example, when $R^2$ is benzyl, it may be possible to carry out the decomposition by reductive means, for example, by the use of hydrogen at a pressure of about thee bars in the presence of a suitable catalyst, such as palladium or platinum, conveniently on charcoal as a support.

A starting material amino ketone of formula V may be obtained from a corresponding alcohol of formula XVI via a corresponding ketone of formula VIII. Thus, by using an oxidation procedure similar to one described above in method (A), the alcohol of formula XVI may be oxidized to the corresponding ketone of formula VIII, for example, by using Dess-Martin periodinane. Removal of the N-protecting group from the ketone of formula VIII will then provide the starting material amino ketone of formula V. The protecting group conveniently may be removed using, for example, trifluoromethanesulfonic acid in dichloromethane at room temperature. It is convenient to isolate an amino ketone of formula V so prepared as its crude trifluoromethanesulfonic acid salt and use it directly for the preparation of a corresponding product of formula I. If an amino ketone of formula V is isolated in the form of its free base, it may be preferable to use the material at once because of the limited stability of the free base.

Starting material ketones of formula IV may also be prepared from an amino ketone of formula V using methods analogous to those described above for the preparation of alcohols of formula VI from an alcohol of formula VII.

As will be clear to one skilled in the art, the order of steps in the sequences leading to the starting materials and products of the invention may be altered if appropriate considerations relative to coupling methods, racemization, deprotection methods, etc. are followed.

INHIBITION MEASUREMENTS

The potency of a compounds of the invention to act as elastase inhibitors is initially determined by the ability of a compound of the invention to inhibit the action of human leukocyte elastase (HLE) on a low molecular weight peptide substrate. The potency of an inhibitor is evaluated by obtaining a kinetic determination of the dissociation constant, $K_i$, of the complex formed from the interaction of the inhibitor with HLE. The substrate used was the anilide methoxy-succinyl-alanyl-alanyl-prolyl-valine-p-nitroanilide as described by Nakajima, K. et al. in *J. Biol. Chem.*, 245, 4027–4032 (1979) and by Teshima, T. et al. in *J. Biol. Chem.*, 257, No. 9, 5085–5091 (1982). The HLE enzyme used in these studies may be obtained from Elastin Products of St. Louis, Missouri or can be purified according to Viscarello, B. R. et al. in *Preparative Biochemistry*, Vol. 13, pages 57–67, (1983) as also described in European Patent Application, Publication Number 204 571 A2. From the thus purified HLE, a standard rate of production of p-nitroaniline was measured at 25° C. spectrophotometrically in the visible spectrum at 410 nanometers with automatic data acquisition from a a Cary 210 spectrophotometer obtained from Varian Associates. Reactions were initiated by injection of 10 microliters of the HLE solution into a 3 milliliter cuvette containing 2.89 milliliters of buffer (10 millimolar sodium phosphate, 500 millimolar NaCl, pH 7.6), 50 microliters substrate solution in DMSO, and 50 microliters of DMSO. Initial, steady-state reaction velocities of p-nitroaniline production were calculated by a fit of the experimental data to a linear dependence on time by linear least squares. This velocity, determined with no inhibitor present, was used as a standard in the calculation of inhibitor $K_i$ values.

If the peptide derivatives of the present invention are found to be "slow-binding" inhibitors of HLE, special methods of analysis to accurately determine $K_i$ values for their inhibition of HLE are carried out (see Williams, J. W. and Morrison, J. F., *Meth. Enz.* 63, 437 (1979) for a description of these methods.) In a typical experiment, 2.89 ml of buffer (10 millimolar sodium phosphate, 500 millimolar sodium chloride, pH 7.6), 50 microliters of inhibitor solution in DMSO, and 50 microliters of substrate solution in DMSO are added to a 3 milliliter cuvette. The cuvette is stoppered, inverted several times to mix its contents and maintained at (25° C.) in the spectrophotometer. After a period of five minutes to allow the reaction solution to come to thermal equilibrium, 10 microliters of stock enzyme solution are added to the cuvette to initiate the reaction. Duplicate or triplicate runs are done at zero inhibitor concentration and at least the non-zero inhibitor concentrations. $K_i$ values are calculated according to methods outlined in the above reference by Williams and Morrison. The $K_i$ values for selected compounds are less than $10^{-7}$M.

ANIMAL MODELS

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model was used.

Hamsters are first lightly anesthetized with Brevital. Phosphate buffered saline (PBS) pH 7.4, either alone or containing 400 µg of human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them either with or at various times prior to administration of HLE to determine their utility in preventing an HLE lesion. Compounds of this invention produced statistically significant reductions in wet lung weight and total lavagable cells relative to HLE alone.

Compounds of the present invention which were tested exhibited activity in at least one of the tests described above under Inhibition Measurement or Animal Model. It should be noted that there was not always a direct correlation between the activities of the compounds measured as $K_i$ values in the Inhibition Measurement test and the reduced values for total lavagable cells and wet lung weights relative to the administration of HLE alone obtained in the Animal Model test.

According to a further feature of the invention there are provided pharmaceutical compositions comprising a pharmaceutically effective amount of at least one substituted ketone of formula I and a pharmaceutically acceptable diluent or carrier.

The compounds of the present invention may be administered to a warm-blooded animal, particularly a human, in need thereof for treatment of a disease in which HLE is implicated, including treatment of a tissue degenerative disease, in particular for the treatment of emphysema. The preferred mode of administration may be via a powdered or liquid aerosol In a powdered aerosol, compounds of the invention may be administered in the same manner as cromolyn sodium via a 'Spinhaler' (a trademark) turbo-inhaler device obtained from Fisons Corp. of Bedford, Massachusetts at a rate of about 0.1 to 50 mg per capsule, 1 to 8 capsules being administered daily for an average human. Each capsule to be used in the turbo-inhaler contains the required amount of a compound of the invention with the remainder of the 20 mg capsule being a pharmaceutically acceptable carrier such as lactose. In a liquid aerosol, the compounds of the invention are administered at the rate of about 100 to 1000 micrograms per "puff" or activated release of a standard volume of propellant. The liquid aerosol would be given at the rate of 1 to 8 puffs per day with variation in dosages due to the severity of the conditions being treated, the weight of the patient and the particular size distribution of the aerosol since smaller particles will achieve greater lung penetration. Propellants, e.g., a fluorinated hydrocarbon or isobutane, containers, valves and actuators for liquid aerosols are described by L. Lachman et al. in "The Theory and Practice of Industrial Pharmacy," Lea and Febiger, Philadelphia (1976).

Alternatively, the mode of administration may be oral or parenteral, including subcutaneous deposit by means of an osmotic pump. The compounds of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 ml intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

The invention will now be illustrated by the following non-limiting examples in which, unless stated otherwise:

(i) temperatures are given in degrees Celsius (C); operations were carried out at room or ambient temperature, that is, at a temperature in the range of 18-°25° C.:

(ii) evaporation of solvent was carried out using a rotary evaporator under reduced pressure (600–4000 pascals; 4.5–30 mm Hg) with a bath temperature of up to 60° C.;

(iii) flash chomatography was carried out on Merck Kieselgel (Art 9385) [obtained from E. Merck, Darmstadt, W. Germany]; if "acidic silica gel" is indicated, material custom prepared by J. T. Baker Chemical Co., Phillipsburg, N.J., USA, and having a pH of about 6 when slurried in water was used; thin layer chomatography (TLC) was carried out on Analtech 0.25 mm silica gel GHLF plates (Art 21521), obtainable from Analtech, Newark, Del. USA:

(iv) in general, the course of reactions was followed by TLC and reaction times are given for illustration only;

(v) melting points are uncorrected and (d) indicates decomposition; the melting points given are those obtained for the materials prepared as described: polymorphism may result in isolation of materials with different melting points in some preparations;

(vi) final products had satisfactory nuclear magnetic resonance (NMR) spectra and were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 80 MHz or 250 MHz using $CDCl_3$, $DMSO-d_6$ or $CD_3OD$ as solvent; conventional abbreviations for signal shape are used, for example: s, singlet; d, doublet; m, multiplet: br, broad: etc.; in addition "Ar" signifies an aromatic group or signal:

(ix) reduced pressures are given as absolute pressures in pascals (Pa): other pressures are given as gauge pressures in bars;

(x) chemical symbols have their usual meanings; the following abbreviations have also been used: min (minutes), h (hours), v (volume), w (weight): mp (melting point), [liter(s)], ml (milliliters), g [gram(s)], mg [milligram(s)];

(xi) solvent ratios are given in volume: volume (v/v) terms;

(xii) mass spectra (MS) were run with an electron energy of 70 electron volts in the chemical ionization mode using a direct exposure probe; when given, only peaks ten percent of the base, peak and larger are reported: and (xiii) when high pressure liquid chromatography (HPLC) data is reported, $t_R$ (retention time) is given in min, FR (flow rate) is given in ml/min, Col A is a Zorbax (trademark) ODS analytical column (4.6 mm ×25 cm) and Col B is a Phenomenex (trademark) Zorbax (trademark) C-8 analytical column (4.6 mm×35 cm).

NOMENCLATURE: For uniformity and clarity, "amino acid sequence" type names are used whenever possible. In general, a stereochemical identification as (S) indicates that the product is estimated to contain at least 95% of the (S)-isomer at the center indicated: the absence of an identification of stereochemistry at a chiral center indicates a mixture of isomers which is not necessarily 1:1 at the center indicated.

EXAMPLE 1

(S)-[4-[(4-Chlorophenyl)sulfonylaminocarbonyl]benzoyl]-L-valyl-Nα-cyclopentyl-N-[3,3-difluoro-1-(1-methylethyl)-2,4-dioxo-4-(propylamino)butyl]glycinamide.

Method A

A solution of the alcohol product from Example 1.m. (0.65 g) in dichloromethane (10 ml) was treated with Dess-Martin periodinane (1.03 g) followed by trifluoroacetic acid (0.062 ml). The mixture was stirred overnight and evaporated, and the residue was partitioned between ethyl acetate and 1:1 (v/v) saturated aqueous $NaHCO_3$:saturated aqueous $Na_2S_2O_3$. The organic phase was washed (10% HCl), dried ($MgSO_4$) and evaporated. Flash chromatography, eluting with chloroform:methanol:acetic acid (100:3:0.5), gave the title compound as a white foam (0.55 g, 87%) after concentration from dichloromethane:hexanes and overnight drying in a vacuum oven; MS(CI), m/e=782(M+1, $^{35}$Cl), 362(base).

Analysis for $C_{36}H_{46}ClF_2N_5O_8S$:
Calculated: C, 55.27: H, 5.93; N, 8.95.
Found: C, 54.99; H, 5.97; N, 8.68.

The alcohol starting material used for Example 1, Method A was prepared as follows:

a. N-Cyclopentylglycine t-butyl ester

A solution of t-butyl bromoacetate (102.43 g) in tetrahydrofuran (100 ml) was added dropwise to a stirred solution of cyclopentylamine (56.21 g) and triethylamine (105 ml, about 76 g) in tetrahydrofuran (500 ml) maintained in the temperature range −5° C. to 0° C. The stirred reaction mixture was allowed to warm to room temperature overnight. The white solid triethylamine hydrobromide was removed by filtration, and the filter cake washed thee times with ethyl acetate. The organic filtrate was evaporated, and the residue was partitioned between water and ethyl acetate. The separated organic layer was washed (water, brine), dried ($MgSO_4$), and evaporated to give a residue which was purified by fractional distillation to yield the product as a colorless liquid (76.43 g): bp 54°-65° C. (49 Pa); TLC, $R_f$=0.18, hexane:ethyl acetate (9:1); MS, m/e=200(M+1), 172, 145, 144(base), 142, 98, 76.

b. Benzyloxycarbonyl-L-valyl-N-cyclopentylglycine t-butyl ester

To a solution of N-benzyloxycarbonyl-L-valine (50.0 g) and N-cyclopentylglycine t-butyl ester (39.8 g) in dichloromethane (1.3 liter), stirred under nitrogen and cooled in an ice bath to 0°-5° C., was added triethylamine (44.5 g) then bis(2-oxo-3-oxazolidinyl)phosphinic chloride (56.0 g) at 0° C. The stirred mixture was allowed to warm to room temperature overnight before it was evaporated. After the residue was partitioned between water (1 liter) and ethyl acetate (1 liter), the ethyl acetate solution was washed (1N hydrochloric acid (twice), water, saturated sodium bicarbonate, brine), dried ($MgSO_4$) and evaporated. The residue was purified by flash chromatography, eluting with ethyl acetate:dichloromethane (0:100, 5:95, 10:90 and 25:75, successively). A first, mixed fraction was rechromatographed and the product obtained combined with the product obtained from the first chromatography to afford the ester (73.4 g, 85%); TLC, $R_f$=0.30, ethyl acetate:dichloromethane (5:95); MS, m/e=433 (M+1), 377, 325, 269, 234, 286, 162, 144 91(base).

c. Benzyloxycarbonyl-L-valyl-N-cyclopentylglycine

To a solution of benzyloxycarbonyl-L-valyl-N-cyclopentylglycine t-butyl ester (73.4 g) in dichloromethane (250 ml), stirred under nitrogen and cooled in an ice bath, was added trifluoroacetic acid (250 ml). After about 5 min the ice bath was removed, and the stirred reaction mixture was allowed to warm to room temperature. After 2.5 h, when TLC indicated complete reaction, the mixture was partially evaporated, removing the dichloromethane and most of the trifluoroacetic acid. The liquid residue was then poured into vigourously stirred ice water, and the resulting mixture of the gummy white solid and aqueous solution was extracted with dichloromethane. The dichloromethane solution was washed (water), diluted with toluene, and evaporated at about 30° C. After several dilutions with toluene, and evaporations to remove traces of water and trifluoroacetic acid, the residue was flash chromatographed on acidic silica gel, eluting with methanol:ethyl acetate:dichloromethane (gradient, 0:0:100, 0:5:95, 0:10:90, 0:25:75, 5:25:70 and 10:25:65, successively) to afford the acid as a white foam (60.4 g, 95%); TLC, $R_f$=0.49, ethyl acetate:dichloromethane:acetic acid (50:50:1); MS, m/e=337(M+1), 359, 225, 91(base).

d. N-Benzyloxycarbonyl-L-valinol

Benzyl chloroformate (91.0 g, 95% purity) was added dropwise over a period of 1 h to a precooled (0° C.) solution of L-valinol (50.0 g) and triethylamine (60.0 g) in chloroform (1500 ml). The reaction mixture was stirred for 1 h at 0° C. and then allowed to warm to,- room temperature over 2 h. After the reaction mixture was evaporated, ethyl acetate (1500 ml) was added to the residue and the organic solution was washed (1N NaOH, brine), dried ($MgSO_4$), and evaporated. The residue was purified by flash chromatography, using a stepwise gradient elution of ether:hexane (1:5) followed by ether, to give the alcohol (91.4 g) as a white waxy solid; TLC, $R_f$=0.23, hexane:ethanol (50:50).

e. N-Benzyloxycarbonyl-L-valinal

A solution of dimethylsulfoxide (107.2 g) in dichloromethane (150 ml) was added dropwise over 0.5 h to a pre-cooled (−60° C.), stirred solution of oxalyl chloride (87.1 g) in dichloromethane (800 ml) under a nitrogen atmosphere. The temperature of the mixture rose to −45° C. The reaction mixture was then warmed to −30° C. A solution of the product of Example 1.d. (81.5 g) in dichloromethane (300 ml) was added dropwise over 45 min at −30° C. The reaction mixture was stirred for 50 min at −25° C., cooled to −40° C. and a solution of diisopropylethylamine (177.4 g) in dichloromethane (250 ml) was added dropwise over 45 min at −40° C. The reaction mixture was stirred for 1 h as it warmed to room temperature. The reaction mixture was diluted with dichloromethane (1500 ml), and the organic phase was washed (1N HCl) and evaporated to give the aldehyde (98 g) as a green oil which was used immediately without further purification: TLC, $R_f$=0.48, hexane:ether (50:50).

f. Ethyl (4S)-4-(benzyloxycarbonyl)amino-2,2-difluoro-3-hydroxy-5-methylhexanoate.

Zinc dust (10 g) was activated by stirring in 3N HCl (250 ml) for 10 min. The material was collected by suction filtration through a sintered glass funnel and was washed successively with water, acetone and dry tetrahydrofuran. The zinc was then dried in a vacuum oven at 40° C. for 2 hours prior to use. A total of 5.93 g of activated, dried zinc was obtained.

A mixture of the aldehyde from Example 1.e. (5.33 g), ethyl 2-bromo-2,2-difluoroacetate (5.75 g), activate zinc (2.22 g) and dry tetrahydrofuran (100 ml) under a nitrogen atmosphere was stirred and sonicated for 2 h. Additional 2-bromo-2,2-difluoroacetate (2 g) was added and sonication along with stirring were continued for 1.5 h. Unreacted zinc was removed by filtration through diatomaceous earth and the filtrate was evaporated. The residue was taken up in ethyl acetate, washed (saturated aqueous $NH_4Cl$, concentrated $NaHSO_3$), dried ($Na_2SO_4$) and evaporated to give the crude product as an oil (7.31 g). Purification by flash chromatography, using a gradient elution of hexane:ethyl acetate (8:1, 4:1, 3:1), gave the ester as an oil containing a 4:1 mixture of isomers (3.56 g; 44%); TLC: $R_f=0.30$ (major isomer), 0.23 (minor isomer), hexane:ethyl acetate (3:1).

f-1 The ester of Example 1.f. was also prepared without sonication as follows:

The aldehyde of Example 1.e. (3.0 g), ethyl 2-bromo-2,2-difluoroacetate (2.58 g), and zinc dust (1.22 g) were refluxed in THF (30 ml) for 0.5 h under nitrogen. Additional zinc dust (1.22 g) and ethyl 2-bromo-2,2-difluoroacetate (2.58 g), were added and the resulting solution refluxed for an additional hour. The solution was cooled to room temperature and ethyl acetate (150 ml) was added. The ethyl acetate solution was washed (1M $KHSO_4$, brine), dried ($Na_2SO_4$) and evaporated to give a crude product (2.4 g). The product was purified by flash chromatography, eluting with ethyl acetate:hexane (35:65) to give the ester (0.9 g) as an oil; TLC, $R_f=0.55$, ethyl acetate:hexane (35:65).

g. (4S)-4-(Benzyloxycarbonyl)amino-2,2-difluoro-3-hydroxy-5-methyl-N-propylhexanamide.

A stirred solution of ester alcohol isomers prepared according to the procedure of Example 1.f. (1.72 g) and n-propylamine (0.57 g) in anhydrous ethanol (40 ml) was heated with an oil bath at 40° C. for 3 h. Additional n-propylamine (0.57 g) was added and heating continued for 1.5 h. The mixture was allowed to cool with stirring overnight. The mixture was evaporated and the residue was taken up in ethyl acetate. This solution was washed (10% HCl, brine), dried ($MgSO_4$) and evaporated to a semi-solid mixture. Upon addition of 3:1 hexane:ethyl acetate, some of the crude product went into solution while a white solid was left behind. The solid was collected by suction filtration and was dried under high vacuum to give material corresponding to the minor hydroxy amide isomer (0.17 g, 10%). The filtrate was concentrated and the residue was purified by flash chromatography, eluting with hexane:ethyl acetate (3:1), to give the pure major hydroxy amide isomer as a colorless gum (1.07 g; 60%) after drying under high vacuum; TLC; $R_f=0.27$ (major isomer), 0.21 (minor isomer), hexane:ethyl acetate (3:1): MS(CI): (major isomer) m/e=373(M+1, base), 329: (minor isomer) m/e=373(M+1), 329(base), 265.

h. (4S)-4-Amino-2,2-difluoro-3-hydroxy-5-methyl-N-propylhexanamide propylhexanamide.

A mixture of the major isomer produced in Example 1.g. (1.05 g) and 10% (w/w) palladium on carbon (0.43 g) in anhydrous ethanol (40 ml) was stirred under 1 bar of hydrogen for 3.5 h. Catalyst was removed by suction filtration through diatomaceous earth. The filtrate was concentrated to an oil which was taken up in a mixture of dichloromethane:hexane, evaporated and dried under high vacuum to leave the amine as a white solid (0.64 g, 96%); MS(CI), m/e=239(M+1, base).

i. (1S)-(Benzyloxycarbonyl)-L-valyl-Nα-cyclopentyl-N-[3,3-difluoro-2-hydroxy-1-(1-methylethyl)-4--oxo-4-(propylamino)butyl]glycinamide The product of Example 1.c. (0.98 g), the product of Example 1.h. (0.62 g) and 1-hydroxybenzotriazole (0.70 g) were dissolved in dry tetrahydrofuran under nitrogen. The solution was treated with 1-(3-dimethylaminopropyl)-3-ethylcarbodiimide hydrochloride (0.55 g) and the mixture was stirred overnight. The mixture was evaporated and the residue was partitioned between water and ethyl acetate. The organic phase was washed (10% HCl, saturated $NaHCO_3$, brine), dried (Na , and evaporated to afford the crude product. Flash chromatography, eluting with chloroform:methanol (80:1), gave the purified alcohol as a white foam (0.89 g) after evaporation from dichloromethane:hexane and overnight drying under high vacuum; TLC, $R_f=0.40$, dichloromethane:methanol (40:1); MS(CI), m/e=597(M+1), 579, 359(base).

j. (1S)-L-Valyl-Nα-cyclopentyl-N-[3,3-difluoro-2-hydroxy-1-(1-methylethyl)-4-oxo-4-(propylamino)-butyl]glycinamide.

The benzyloxycarbonyl protecting group in the product of Example 1.i. (0.87 g) was removed by application of the procedure of Example 1.h. (using 40 ml ethanol and 0.48 g 10% palladium on carbon). The amine was isolated as a white foam (0.68 g, 100%) after evaporation from dichloromethane:hexane and drying under high vacuum; TLC, $R_f=0.16$, chloroform:methanol (40:1).

k. 1,1-Dimethylethyl 4-[(4-chlorophenyl)sulfonylaminocarbonyl]benzoate

A 5-liter, 3-necked, round-bottomed flask was equipped with a mechanical stirrer and nitrogen inlet. dichloromethane (2 liters) was placed in the reaction flask and terephthalic acid mono-t-butyl ester (127.5 g), 4-dimethylaminopyridine (70.06 g), and 4-chlorobenzenesulfonamide (110.04 g) were added in that order using dichloromethane (400 ml) to wash down the solids. 1-(3-Dimethylaminopropyl)-3-ethylcarbodiimide hydrochloride (110.10 g) was added in portions over 10 min using dichloromethane (100 ml) to wash down the solid. After the reaction mixture was stirred overnight at room temperature, it was evaporated. The residue was partitioned between ethyl acetate and water. The organic solution was washed (20% (w/v) aqueous citric acid, saturated aqueous $NaHCO_3$, brine), dried ($Na_2SO_4$), and evaporated to a white solid. After drying in a vacuum oven at 50° C., the ester (227 g, 100%) was obtained in a sufficiently pure state to be used directly for the next step; TLC, $R_f$=0.43, methanol:chloroform (15:85). (Further purification was possible by recrystallization from ethanol:water; mp above 300° C.).

1. 4[(4-Chlorophenyl)sulfonylaminocarbonyl]benzoic acid.

A 3-liter, 3-necked, round bottomed flask was equipped with a mechanical stirrer and a $CaCl_2$ drying tube. Trifluoroacetic acid (1300 g) was added and cooled to 0° C., and the product of Example 1.k. (79.5 g) was added. Initially, the solid dissolved, giving a clear solution. After 10–15 min, a heavy precipitate of product formed; and it was difficult to stir the reaction mixture. Vigorous stirring with the mechanical stirrer was essential to drive the reaction to completion. The reaction mixture was stirred at 0°–5° C. for 1 h before it was poured onto 1500 ml of ice/water and stirred for 2 h. The resulting solid was filtered and dried. The white solid (61.5 g, 91%) obtained was recrystallized from 1600 ml absolute ethanol/1600 ml water to yield the acid (54 g, 80%) as white needles; mp 286°–288° C.; TLC, $R_f$=0.7, methanol:chloroform:acetic acid (10:90:1).

m.
(1S)-[4-[(4-Chlorophenyl)sulfonylaminocarbonyl]-benzoyl]-L-valyl-Nα-cyclopentyl-N-[3,3-difluoro-2-hydroxy-1-(1-methylethyl)-4-oxo-4-(propylamino) butyl)glycinamide.

A dry tetrahydrofuran solution of the product of Example 1.1. (0.49 g), the product of Example 1.g. (0.67 g) and 1-hydroxybenzotriazole (0.39 g) was treated with 1-(3-dimethylaminopropyl)-3-ethylcarbodiimide hydrochloride (0.31 g) and stirred under nitrogen overnight. Workup as in Example 1.i. gave the crude product. Flash chromatography, eluting with chloroform:methanol:acetic acid (gradient, 200:5:1, 200:8:1), afforded the alcohol as a white foam (0.66 g; 57%) after evaporation from dichloromethane:hexane and high vacuum drying; TLC, $R_f$=0.35, chloroform: methanol:acetic acid (100:5:0.5); MS(CI), m/e=784(M+1, $^{35}$Cl, base), 766.

Method B

The product of Example 1 was also prepared with minimal purification of intermediates as follows:

A solution of the product from Example 1.r. (0.44 g) in dichloromethane (6 ml) was treated with Dess-Martin periodinane (1.19 g) followed by trifluoroacetic acid (0.22 ml). The mixture was stirred overnight, diluted with ethyl acetate and stirred with 1:1 (v/v) saturated $NaHCO_3$:saturated $Na_2S_2O_3$. The organic phase was washed (10% HCl), dried ($Na_2SO_4$) and evaporated to give a yellow solid (0.37 g). Flash chromatography, eluting with hexane:ethyl acetate:acetic acid (50:50:1), gave the title compound as a white solid (0.15 g, 34%) after concentration from hexane/dichloromethane and overnight drying in a vacuum oven.

Analysis for $C_{36}H_{46}ClF_2N_5O_8S$:
Calculated: C, 55.27; H, 5.93; N, 8.95.
Found: C, 55.58; H, 6.15; N, 8.48.

The alcohol starting material used for Example 1, Method B was prepared as follows:

n.
(4S)-4-(Benzyloxycarbonyl)amino-2,2-difluoro-3-hydroxy-5-methyl-N-propylhexanamide.

A mixture of ester alcohol isomers prepared according to the procedure of Example 1.f. (1.4 g) and n-propylamine (0.48 g) in anhydrous ethanol (40 ml) was stirred overnight under nitrogen. More n-propylamine (0.86 g) was added, and stirring was continued for several hours. The reaction mixture was heated to reflux for 45 min, cooled and worked up according to the procedure given in Example 2.a. Trituration with hexane:ethyl acetate (3:1) gave a white solid (0.33 g, 23%) substantially enriched in minor product isomer. Flash column chromatography of the evaporated supernatant, eluting with hexane:ethyl acetate (3:1), gave two product fractions which were combined to yield additional amide as an oil (0.53 g, 37%) substantially enriched in the major product isomer.

o.
(4S)-4-Amino-2,2-difluoro-3-hydroxy-5-methyl-N-propylhexanamide hydrochloride The amide enriched in the major isomer produced in Example 1.n. (0.53 g) was dissolved in anhydrous ethanol (10 ml). To the solution were added 10% (w/w) palladium on carbon (0.10 g) and concentrated HCl (0.36 g). The mixture was stirred under 1 bar of hydrogen for 2 h. Catalyst was removed by suction filtration through diatormaceous earth. The filtrate was evaporated and dried to give the amine hydrochloride an oil (0.36 g, 92%).

p.
(1S)-(Benzyloxycarbonyl)-L-valyl-Nα-cyclopentyl-N-[3,3-difluoro-2-hydroxy-1-(1-methylethyl)-4-oxo-4-(propylamino)butyl]glycinamide The product of Example 1.o. (0.36 g) was taken up in a mixture of dichloromethane (10 ml) and tetrahydrofuran (3 ml). To this solution were sequentially added material prepared according to Example 1.c. (0.49 g), 1-hydroxybenzotriazole (0.35 g), 1-(3-dimethylaminopropyl)-3-ethylcarbodiimide hydrochloride (0.25 g) and 4-methylmorpholine (0.15 ml). The mixture was stirred overnight under nitrogen, diluted with dichloromethane, washed (saturated $NaHCO_3$, 10% HCl), dried ($Na_2SO_4$) and evaporated to an oil (0.70 g, 90%) which was used in the next step without further purification; TLC, intense product spots at Rf=0.19, 0.23, chloroform:methanol, (50:1).

q.
(1S)-L-Valyl-Nα-cyclopentyl-N-[3,3-difluoro-2-hydroxy-1-(1-methylethyl)-4-oxo-4-(propylamino)-butyl]glycinamide.

A mixture of the product from Example 1.p. (0.70 g) and 10% (w/w) palladium on carbon (0.10 g) in ethanol (10 ml) was stirred under 1 bar of hydrogen until the starting material was all consumed as judged by TLC. Catalyst was removed by filtration through diatomaceous earth and the filtrate was concentrated to a foam/glass (0.34 g, 63%). This material was used in the next step without further purification.

r.
(1S)-[4-[(4-Chlorophenyl)sulfonylaminocarbonyl]-benzoyl]-L-valyl-Nα-cyclopentyl-N-[3,3-difluoro-2-hydroxy-1-(1-methylethyl)-4-oxo-4-(propylamino) butyl]glycinamide A dichloromethane (6 ml) solution of the product of Example 1.q. (0.34 g), the product of Example 1.1. (0.25 g) and 1-hydroxybenzotriazole (0.20 g) was treated with 1-(3-dimethylaminopropyl)-3-ethylcarbodiimide hydrochloride (0.14 g) and stirred under nitrogen overnight. The mixture was diluted with ethyl acetate, washed (saturated $NaHCO_3$, 10% HCl), dried ($Na_2SO_4$)

and evaporated to a glass (0.44 g, 76%) which was used without further purification; TLC: $R_f=0.59$, chloroform:methanol (10:1, with a trace of acetic acid).

EXAMPLE 2

(S)-[4-[(4-Chlorophenyl)sulfonylaminocarbonyl]benzoyl]-L-valyl-Nα-cyclopentyl-N-[3,3-difluoro-1-(1-methylethyl)-2,4-dioxo-4-[(2-phenylethyl)amino]butyl]-glycinamide.

A solution of the alcohol from Example 2.e. (0.34 g) in dichloromethane (5 ml) was treated with Dess-Martin periodinane (0.85 g) followed by trifluoroacetic acid (0.15 ml). The reaction was stirred overnight, diluted with ethyl acetate, and stirred with a 1:1 (v/v) mixture of saturated NaHCO$_3$ and saturated Na$_2$S$_2$O$_3$. The organic phase was isolated, washed (10% HCl), dried (Na$_2$SO$_4$) and evaporated to give a glass (0.30 g). Flash chromatography, eluting with hexane:ethyl acetate:acetic acid (50:50:1), gave the title compound as a white solid (0.14 g); MS(CI), m/e=844(M+1), 546, 424(base).

Analysis for C$_{41}$H$_{48}$ClF$_2$N$_5$O$_8$S.0.6 H$_2$O:
Calculated: C, 57.58; H, 5.80; N, 8.19.
Found: C, 57.55; H, 5.64; N, 8.16.

The alcohol starting material used for Example 2 was prepared as follows:

a.
(4S)-4-(Benzyloxycarbonyl)amino-2,2-difluoro-3-hydroxy-4-methyl-N-(2-phenylethyl)hexanamide A stirred solution of ester alcohol isomers prepared according to the procedure of Example 1.f. (1.4 g) and phenethylamine (0.94 g) in anhydrous ethanol (40 ml) was stirred overnight. Because starting material was still evident by TLC, more phenethylamine (1 g) was added and stirring was continued for several hours. Because no appreciable change in the TLC was noted, the reaction was heated to gentle reflux and was held there for 45 min. The reaction mixture was cooled, evaporated and the residue taken up in ethyl acetate. The organic solution was washed (10% HCl), dried (NaSO$_4$) and concentrated to a semisolid mixture (1.63 g). A 3:1 mixture of hexane:ethyl acetate was added, dissolving some of the crude product while leaving behind a white solid. The solid was collected by suction filtration and was dried under high vacuum to give material substantially enriched in the minor hydroxy amide isomer (0.46 g, 27%). The filtrate was concentrated and the residue was purified by flash chromatography, eluting with hexane:ethyl acetate (3:1), to give, after drying under high vacuum, an oil substantially enriched in the major hydroxy amide isomer (0.55 g, 33%); TLC, $R_f=0.22$ (major isomer), 0.17 (minor isomer), hexane:ethyl acetate (3:1): MS(CI), (major isomer) m/e=435(M+1), 391(base), 327; (minor isomer) m/e=435(M+1), 391(base), 327, 91.

b.
(4S)-4-Amino-2,2-difluoro-3-hydroxy-4-methyl-N-(2-phenylethyl)hexanamide hydrochloride The material enriched in the minor isomer produced in Example 2.a. (0.44 g) was dissolved in anhydrous ethanol (40 ml). To the solution were added 10% (w/w) palladium on carbon (90 mg) and concentrated HCl (0.35 g). The mixture was stirred under 1 bar of hydrogen overnight. Catalyst was removed by suction filtration through diatomaceous earth. The filtrate was evaporated and dried to give the amine hydrochloride as a white solid (0.33 g, 93%).

c.
(1S)-(Benzyloxycarbonyl)-L-valyl-Nα-cyclopentyl-N-[3,3-difluoro-2-hydroxy-1-(1-methylethyl)-4-oxo-4-[(2-phenylethyl)amino]butyl]glycinamide.

The product of Example 2.b. (0.33 g) was taken up in a mixture of dichloromethane (7 ml) and tetrahydrofuran (5 ml). Sequential addition of the product of Example 1.c. (0.36 g), 1-hydroxybenzotriazole (0.27 g), 1-(3-dimethylaminopropyl)-3-ethylcarbodiimide hydrochloride (0.18 g) and 4-methylmorpholine (0.10 ml) was followed by overnight stirring of the reaction mixture under nitrogen. The mixture was diluted with dichloromethane, washed (saturated NaHCO$_3$, 10% HCl), dried ) and evaporated to afford crude alcohol as a glass/foam (0.50 g, 79%); TLC, $R_f=0.57$, chloroform:methanol (10:1). This material was used in the next step without further purification.

d.
(1S)-L-Valyl-Nα-cyclopentyl-N-[3,3-difluoro-1-hydroxy-1-(1-methylethyl)-4-oxo-4-[(2-phenylethyl)amino]butyl]glycinamide A mixture of the product of Example 2.c. (0.50 g) and 10% (w/w) palladium on carbon (0.10 g) in ethanol (10 ml) was stirred under 1 bar of hydrogen for 1.5 h. Catalyst was removed by filtration through diatomaceous earth and the filtrate was evaporated to afford the amino alcohol as a glass (0.30 g, 75%); TLC, two fluorescamine active spots, $R_f=0.37$ and 0.40, chloroform:methanol (1:1). This material was used in the next step without further purification.

e.
(1S)-[4-[(4-Chlorophenyl)sulfonylaminocarbonyl]-benzoyl]-L-valyl-Nα-cyclopentyl-N-[3,3-difluoro-2-hydroxy-1-(1-methylethyl)-4-oxo-4-[(2-phenylethyl)amino]butyl]glycinamide A dichloromethane (5 ml) solution of the product of Example 2.d. (0.30 g), the product of Example 1.1. (0.19 g) and 1-hydroxybenzotriazole (0.15 g) was treated with 1-(3-dimethylaminopropyl)-3-ethylcarbodiimide hydrochloride (0.11 g) and stirred under nitrogen overnight. The mixture was diluted with dichloromethane, washed (saturated NaHCO$_3$, 10% HCl), dried (Na$_2$SO$_4$) and evaporated to give the alcohol as a yellow solid (0.34 g, 72%), which exhibited two major components by TLC and was used without further purification; TLC, $R_f=0.52$, 0.62, chloroform:methanol (10:1 with a trace of acetic acid).

FORMULAE

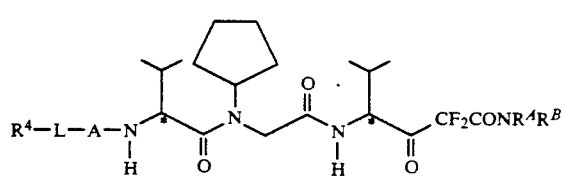

I

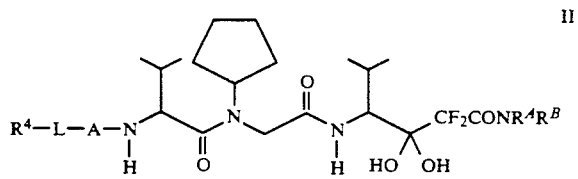

II

-continued
FORMULAE
III
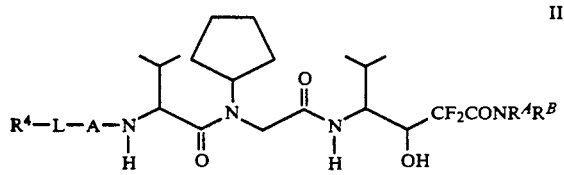
IV
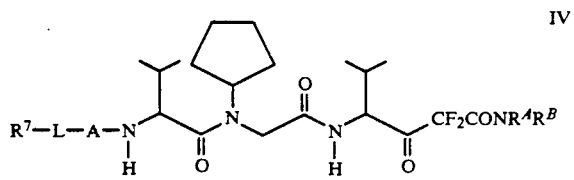
-continued
FORMULAE
V
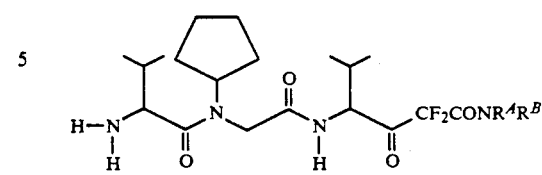
VI
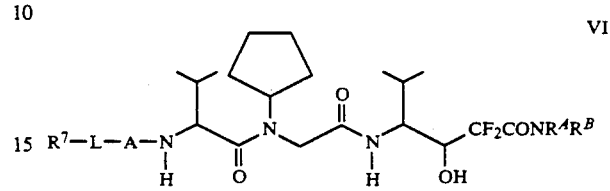
SCHEME I
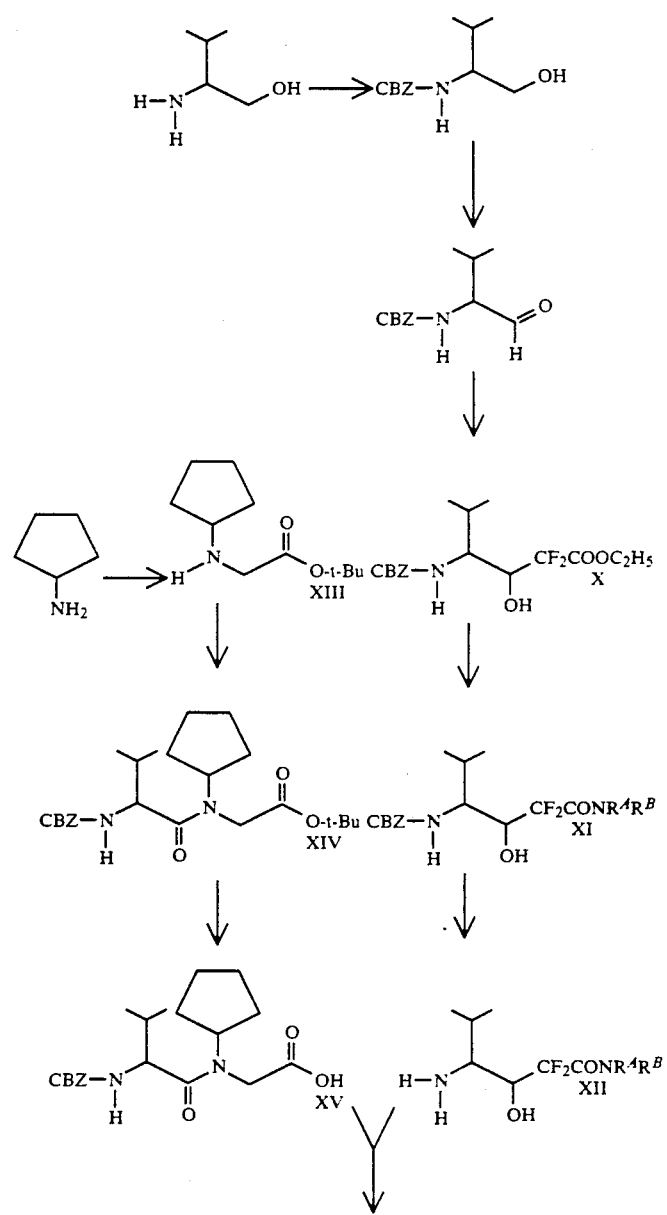

SCHEME I

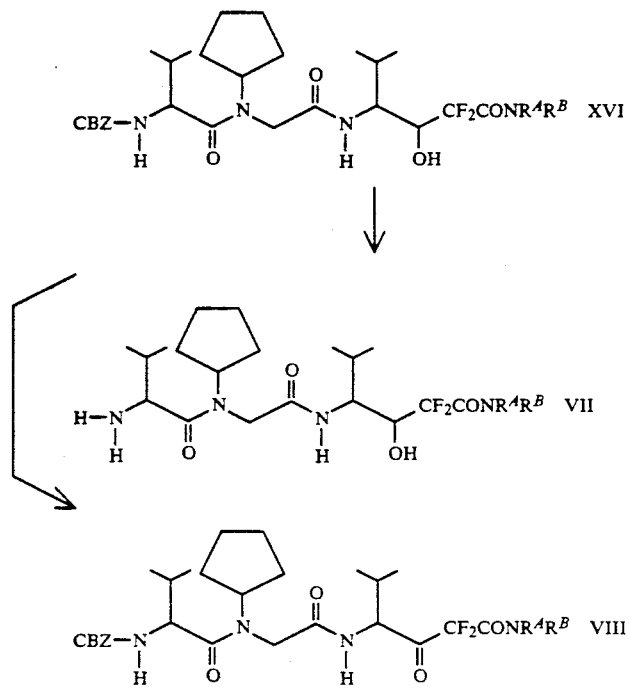

-continued

What is claimed is:

1. A compound of formula I, formula set out hereinbelow, wherein:

A is selected from a group consisting of —CO—, —NH.CO— and —O.CO—;

L is selected from a group consisting of phenylene, (1-6C)alkanediyl, (2-6C)alkenediyl and phenylene (1-3C)alkyl, optionally containing one double bond in the alkyl portion, with the condition that no carbon included in a double bond of an alkenediyl group or included in an optional double bond of a phenylenealkyl group be directly bonded to an oxygen or nitrogen atom of group A;

$R^4$ is selected from a group consisting of acylsulfonamide of formula $R^5.S(O_2).NH.CO$—, acrysulfonamide of formula $R^5.CO.NH.S(O_2)$—, sulfonylurea of formula $R^5.NH.CO.NH.S(O_2)$—, sulfonylurea of formula $R^5.S(O_2).NH.CO.NR^6$—, and trilfluoromethylsulfonamide of formula $CF_3.S(O_2).NH$— wherein $R^5$ is selected from a group consisting of (1-10C)alkyl; trifluoromethyl; (3-10C)cycloalkyl; (6 or 10C)aryl optionally substituted by 1 to 3 members of a group consisting of halogeno, nitro, amino, dimethylamino, hydroxy, methyl, trifluoromethyl, carboxy, phenyl, and {(1-5C)alkylcarbonyl}amino [[(1-5C)alkylcarbonyl]amino]; and an aromatic heterocyclic group which is furyl, thienyl, pyridyl or pyrimidinyl in which up to 3 carbons of the aromatic system may bear a substituent group independently selected from a group consisting of halogeno an trifluoromethyl; and $R^6$ is hydrogen or methyl;

$R^A$ is hydrogen or methyl; and $R^B$ is selected from a group consisting of (1-10C)alkyl, (3-7C)cycloalkyl(1-6C)alkyl (wherein the cycloalkylalkyl group contains no more than about 10 carbon atoms), and a (1-6C)alkyl group bearing a substituent $R^C$ wherein $R^C$ is a phenyl, thienyl or furyl group; or a pharmaceutically acceptable base-addition salt thereof.

2. A compound as claimed in claim 1 wherein:

$R^5$ is methyl, ethyl, propyl, isopropyl, t-butyl, 4-methylpentyl, cyclopropyl, cyclopentyl, cyclohexyl, norbornyl, adamantyl, phenyl or naphthyl, which phenyl or naphthyl may optionally bear a fluoro, chloro, bromo, formylamino, acetylamino, 2-methylpropanoylamino or 2,2-dimethylpropanoylamino substituent; or $R^5$ is furyl, thienyl, pyridyl or pyrimidinyl, which heterocyclic group may optionally bear a fluoro, chloro or bromo substituent;

L is p-phenylene, m-phenylene, methylene, ethan-1,2-diyl, ethan-1,1-diyl, propan-1,3-diyl, propan-1,2-diyl, propan-2,2-diyl, butan-1,4-diyl, 2-methylpropan-2,3-diyl, 2-methylpropan-1,2-diyl, pentan-1,5-diyl, ethen-1,2-diyl, propen-1,2-diyl, propen-1,3-diyl, buten-1,4-diyl, but-2-en-1,4-diyl, penten-1,5-diyl, 3,3-dimethylpropen-1,3-diyl, p-phenylenemethyl, 2-(p-phenylene)ethyl or 2-(p-phenylene)-2-propyl, or 2-(p-phenylene)ethenyl; and $R^B$ is methyl, ethyl, propyl, butyl, 2-methylpropyl, pentyl, 3-methylbutyl, hexyl, cyclopropylmethyl, cyclopentylmethyl, cyclohexylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, benzyl, 2-phenylethyl, 3-phenylpropyl, 4-phenylbutyl, 2-thienylethyl or 2-furylethyl.

3. A compound as claimed in claim 2 wherein in $R^4$ is $R^5.S(O_2).NH.CO$—; L is p-phenylene; A is —CO—; $R^A$ is hydrogen; and $R^B$ is propyl or 2-phenylethyl.

4. A compound as claimed in claim 1, 2 or 3 wherein $R^5$ is phenyl or 4-chlorophenyl.

5. A compound as claimed in claim 1 which is [4-[(4-chlorophenyl)sulfonylaminocarbonyl]benzoyl]-L-valyl-Nα-cyclopentyl-N-[3,3-difluoro-1-(1-methylethyl)-2,4-dioxo-4-(propylamino)butyl]glycinamide.

6. A pharmaceutically acceptable base addition salt as claimed in claim 1 which is a sodium salt.

7. A pharmaceutical composition comprising a compound of any one of claim 1, 2, 3, 5 or 6 in an amount sufficient to inhibit human leukocyte elastase in a living mammal in association with a pharmaceutically acceptable diluent or carrier.

8. A pharmaceutical composition as claimed in claim 7 wherein said composition is in the form of a liquid or powdered aerosol.

9. A method of inhibiting the action of leukocyte elastase in a mammal requiring such treatment comprising administering to said mammal an effective amount of a compound of claim 1.

10. A method of treating emphysema in a mammal comprising administering to the mammal a pharmacologically effective amount of a compound of claim 1.

11. A compound of formula III set out hereinbelow wherein A, L, $R^A$, $R^B$ and $R^4$ have any of the meanings defined in claim 1.

12. A compound of formula IV set out hereinbelow wherein A, L, $R^A$ and $R^B$ have any of the meanings defined in claim 1 and wherein $R^7$ is selected from a group consisting of carboxy, $H_2N.S(O_2)$—, $HNR^6$—, and —NCO and wherein $R^6$ is hydrogen or methyl.

* * * * *

UNITED STATES PATENT AND TRADEMARK OFFICE
CERTIFICATE OF CORRECTION

PATENT NO. : 5,270,301
DATED : December 14, 1993
INVENTOR(S) : Donald J. Wolanin It is certified that error appears in the above-identified patent and that said Letters Patent is hereby corrected as shown below:

Column 21, line 46, delete "acrysulfona-" and insert -- acylsulfona- --.

Column 21, line 58, delete "[[(1-5C)alkylcarbonyl]amino]".

Signed and Sealed this

Sixteenth Day of December, 1997

Attest:

BRUCE LEHMAN

Attesting Officer

Commissioner of Patents and Trademarks